US010602950B2

(12) United States Patent
Ashe et al.

(10) Patent No.: US 10,602,950 B2
(45) Date of Patent: Mar. 31, 2020

(54) MULTIMODAL PROBE ARRAY

(71) Applicants: General Electric Company, Schenectady, NY (US); Brigham Young University, Provo, UT (US)

(72) Inventors: Jeffrey M. Ashe, Gloversville, NY (US); Kaustubh Ravindra Nagarkar, Clifton Park, NY (US); Christopher Michael Puleo, Schenectady, NY (US); Christopher Fred Keimel, Schenectady, NY (US); Craig Patrick Galligan, Schenectady, NY (US); Yizhen Lin, Schenectady, NY (US); Nancy Cecelia Stoffel, Schenectady, NY (US); Richard Vanfleet, Provo, UT (US); Robert Davis, Provo, UT (US); Guohai Chen, Provo, UT (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 476 days.

(21) Appl. No.: 15/377,696

(22) Filed: Dec. 13, 2016

(65) Prior Publication Data
US 2018/0160929 A1 Jun. 14, 2018

(51) Int. Cl.
*A61B 5/0478* (2006.01)
*A61B 5/1473* (2006.01)
*A61B 5/145* (2006.01)
*A61B 7/02* (2006.01)
*A61N 1/05* (2006.01)
(Continued)

(52) U.S. Cl.
CPC .......... *A61B 5/0478* (2013.01); *A61B 5/1473* (2013.01); *A61B 5/14546* (2013.01); *A61B 7/023* (2013.01); *A61N 1/0531* (2013.01); *A61N 1/0534* (2013.01); *A61B 5/11* (2013.01); *A61B 2017/0023* (2013.01); *A61B 2017/00911* (2013.01); *A61B 2562/0209* (2013.01); *A61B 2562/0285* (2013.01); *A61B 2562/06* (2013.01); *A61B 2562/125* (2013.01)

(58) Field of Classification Search
CPC ......................... A61B 5/0478; A61B 5/14546
USPC ........................................................... 607/2
See application file for complete search history.

(56) References Cited

U.S. PATENT DOCUMENTS

| 5,215,088 A | 6/1993 | Normann et al. |
| 7,211,143 B2 | 5/2007 | Yang et al. |
| 8,387,240 B2 | 3/2013 | Muthukumar et al. |

(Continued)

FOREIGN PATENT DOCUMENTS

CN 204637301 U 9/2015

OTHER PUBLICATIONS

Gibson et al. "Neural Biosensor Probes for Simultaneous Electrophysiological Recordings, Neurochemical Measurements, and Drug Delivery with High Spatial and Temporal Resolution", Thesis, pp. 1 to 106, 2011.

(Continued)

*Primary Examiner* — Nadia A Mahmood
(74) *Attorney, Agent, or Firm* — Fletcher Yoder, P.C.

(57) ABSTRACT

The present approach relates to the fabrication and use of a probe array having multiple individual probes. In one embodiment, the probes of the probe array may be functionalized such that certain of the probes are suitable for electrical sensing (e.g., recording) or stimulation, non-electrical sensing or stimulation (e.g., chemical sensing and/or release of biomolecules when activated), or a combination of electrical and non-electrical sensing or stimulation.

18 Claims, 12 Drawing Sheets

(51) Int. Cl.
    *A61B 5/11*      (2006.01)
    *A61B 17/00*     (2006.01)

(56) References Cited

U.S. PATENT DOCUMENTS

| | | |
|---|---|---|
| 8,661,663 B2 | 3/2014 | Wolfe et al. |
| 8,736,138 B2 | 5/2014 | Davis et al. |
| 2007/0067007 A1 | 3/2007 | Schulman et al. |
| 2007/0218202 A1 | 9/2007 | Ajayan et al. |
| 2009/0179354 A1 | 7/2009 | Lizotte |
| 2010/0241100 A1 | 9/2010 | Blumenfeld et al. |
| 2010/0300728 A1 | 12/2010 | Kruglick |
| 2011/0087315 A1 | 4/2011 | Richardson-Burns et al. |
| 2011/0184503 A1 | 7/2011 | Xu et al. |
| 2012/0202347 A1 | 8/2012 | Ready et al. |
| 2013/0085359 A1 | 4/2013 | Yao et al. |
| 2013/0157498 A1 | 6/2013 | Scholvin et al. |
| 2013/0233609 A1 | 9/2013 | Kummerl |
| 2013/0285160 A1 | 10/2013 | Davis et al. |
| 2016/0058316 A1 | 3/2016 | Vitale et al. |
| 2016/0120424 A1 | 5/2016 | Pan et al. |

OTHER PUBLICATIONS

Bareket-Keren, Lilach, et al.; "Carbon nanotube-based multi electrode arrays for neuronal interfacing: progress and prospects", Front Neural Circuits, 6: 122, 2012.

Yoon, Inho, et al.; "Intracellular Neural Recording with Pure Carbon Nanotube Probes", Plos one, Jun. 19, 2013.

MULTIMODAL PROBE ARRAY

TECHNICAL FIELD

Embodiments of the present application generally relate to the use and/or fabrication of a mutimodal probe array, and more particularly, to mutimodal probe array suitable for monitoring neuron activity across multiple signal modalities (e.g., electrical and chemical).

BACKGROUND

Understanding the mechanisms mediating learning and other forms of cortical plasticity at the level of neuronal ensembles could aid in the development of therapies for neurodegenerative disease as well as the design of assistive brain-computer interfaces. However, the relationship between neuronal ensemble activity and the kinetics of cortical neurotransmitter release and clearance are poorly understood. Rodent experiments have highlighted the role of neuromodulators, such as dopamine, in cortical plasticity and learning. Neuromodulators simultaneously engage large numbers of neurons, but their effects on neuronal ensemble activity cannot be readily observed directly. For example, conventional approaches may allow for recording of electrical transmission or stimulation data, but such data does not provide a full picture as chemical sensing and delivery data may be omitted. Conversely, observation along the chemical domain may not allow for obtaining the corresponding electrical data. Using conventional approaches, simultaneous acquisition of such multi-modal data in the site corresponding in size to a neuron or groups of neurons is not feasible.

BRIEF DESCRIPTION

In one embodiment, a probe array structure is provided. In accordance with this embodiment, the probe array structure includes a plurality of probes, wherein each probe comprises a carbon nanotube template. With respect to a first subset of probes of the plurality of probes, the first subset of probes is functionalized with a first material or set of materials such that, when in use, the first subset of probes senses a first physiological property of an underlying tissue or stimulates the underlying tissue. With respect to a second subset of probes of the plurality of probes different from the first subset, the second subset of probes is functionalized with a second material or set of materials such that, when in use, the second subset of probes senses a second physiological property of the underlying tissue or stimulates the underlying tissue.

In a further embodiment, a probe array structure is provided. In accordance with this embodiment, the probe array structure includes a plurality of probes. Each probe comprises a functionalized carbon nanotube template. Each probe is individually electrically addressable such that the activation of each probe is independent of the other probes of the plurality of probes.

In an additional embodiment, a probe array structure is provided. In accordance with this embodiment, the probe array structure includes a plurality of probes. Each probe comprises a carbon nanotube template. Some or all of the probes have magnetic susceptibility matched to biological tissue.

In another embodiment, a probe kit is provided. In accordance with this embodiment, the probe kit includes: a probe array comprising a plurality of individually addressable carbon nanotube probes, each carbon nanotube probe functionalized to sense a physiological property of an underlying tissue or stimulates the underlying tissue when in use; one or more connector pieces configured to interface the probe array with a respective medical device; one or more insertion tools configured to facilitate the placement of the probe array to a target tissue; and one or more surgical tools suitable for performing a surgical procedure for insertion of the probe array.

In a further embodiment, a method of fabricating a probe array is provided. In accordance with this embodiment, on a substrate, a pattern of catalyst pads is formed on respective electrically conductive vias that run through the substrate. A porous carbon nanotube template is grown on each catalyst pad using a chemical vapor deposition. The porous carbon nanotube templates are infiltrated to form respective probes from each porous carbon nanotube template.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1A:
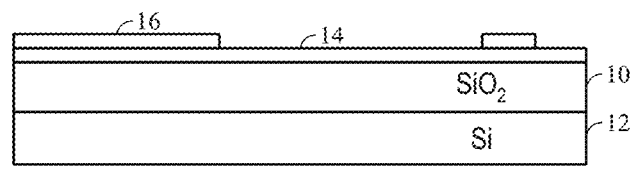
FIGS. 1A, 1B, and 1C depict a graphical process flow of the carbon nanotube formation and template fabrication using CNT-M, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements.

The importance of neural modulation and implant-based therapies continues to increase in the realm of medical treatment and diagnostics. For example, current trends are toward an expansion of the use of deep brain stimulators beyond treatment of Parkinson's disease to other diseases, such as Alzheimer's and depression. Consequently, there is an increasing need for neuroprobes that provide advanced functionality. For example, neuroprobes with the capability to simultaneously stimulate a neural pathway electrically and to measure corresponding changes in neurotransmitter release may allow real-time optimization of probe placement and electrical stimulation parameters. Further, neuroprobes with magnetic susceptibility matched to that of the surrounding tissue may eliminate implant artifacts in MRI images (allowing for more exact positioning of probes within or around neural anatomical structures). In addition, due to the importance of eliminating failures in neural implants and achieving long implant lifetimes, it may be useful for this type of advanced neuroprobe functionality to be built into the probe in a simple manner (i.e., without the need for multiple complex fabrication steps or seams and interfaces between different components and materials within the probe).

With the preceding in mind, the present approach relates to the fabrication and use of a probe array having multiple individual probes (such as individually addressable sensing and/or stimulation probes in the form of functionalized carbon nanotube-based needles). In this example, the probe array may be positioned over an underlying tissue region to be monitored and/or stimulated by the individual probes of the array such that the respective probes of the array are effectively interrogating the same tissue or tissue structure (e.g., a neuron or neural path) despite being separate and distinct from one another. Indeed, different probe types, as discussed herein, may be intermingled with one another in the probe array such that the different types of measurements (or stimulation events) associated with the different probe types cover a co-mingled or intermingled span or range of the underlying tissue. This is in contrast to contexts where separate devices are used to interrogate different but proximate regions of underlying tissue due to the separate and distinct nature of the devices.

By way of example, in one embodiment, the probes of the probe array may be functionalized such that certain of the probes are suitable for electrical sensing (e.g., recording) or stimulation of an underlying tissue while other separately addressable probes are suitable for non-electrical sensing or stimulation (e.g., chemical sensing and/or release of biomolecules when activated) of the underlying tissue. As discussed herein, such a device may be utilized in the study of neural ensemble state dynamics or other complex tissue or other phenomena, such as in situations where detection, measurements, and/or generation of mixed signal types are present. Using sensing devices fabricated in the manner discussed herein, sensing operations (e.g., neural sensing operations) may be performed that incorporate multianalyte chemical monitoring, controlled chemical release, mechanical or acoustic monitoring or stimulation, and/or simultaneous single unit (i.e., electrical) recording. Such sensing devices may be suitable for use in neural or neuromuscular contexts, where concurrent chemical and electrical measurements at a single site are of interest. These devices may be of particular help in the study of diffuse modulatory systems that regulate the activity of widespread populations of neurons where the effects of chemical signals are observed on a broad network (system) level. These devices may also be of interest in therapeutic device (i.e., deep brain stimulators) where simultaneous monitoring of the chemical response to electrical stimulation may aid in electrode placement and optimization of electrical stimulation parameters (e.g. pulse amplitude, frequency, or duration). However, due to the limitations of conventional sensing device technology, linking neuromodulatory signals to information processing in networks of individual neurons remains an outstanding challenge due to the lack of suitable electrical activity recording and chemical sensing technologies.

As may be inferred from the discussion above, such combined concurrent sensing may be of interest in experimental, or other, studies where the relationship between neuronal ensemble activity and the kinetics of cortical neurotransmitter release and clearance are poorly understood. For instance, recent rodent experiments have highlighted the role of neuromodulators such as dopamine in cortical plasticity and learning. Neuromodulators simultaneously engage large numbers of neurons, but their effects on neuronal ensemble activity cannot be observed directly since current multisite electrical recording platforms are not readily coupled with chemical sensing or delivery. In such a context, combined large-scale multisite single unit recording (i.e., electrical sensing) with chemical sensing would add a new dimension to the study of neural ensemble state dynamics. In this example, understanding the mechanisms mediating learning and other forms of cortical plasticity at the level of neuronal ensembles could aid in the development of therapies for neurodegenerative disease as well as the design of assistive brain-computer interfaces.

Further, additional material choices for probe fabrication may also be useful to enable tailoring or otherwise configuring of electrical, mechanical, and magnetic properties. For example, metallic materials which maintain high electrical conductivity often have non-optimal mechanical properties (i.e., they typically do not match the mechanical stiffness of the nerve tissue, causing tissue damage and inflammation). Additionally, there is currently a lack of materials that both match the magnetic susceptibility of human/nerve tissue and remain biocompatible (i.e. capable of use in an implant). Mismatch of magnetic susceptibly between an implant and the surrounding tissue causes large distortions of artifacts in MR images, making viewing or positioning implants with respect to anatomical markers difficult. The ability to tailor material properties (such as mechanical stiffness or magnetic susceptibility) of neuroprobes during fabrication would greatly advance both the science and practice of neuromodulation.

With the preceding in mind, in conventional sensor fabrication technologies, standard and lithographic fabrication techniques are typically planar, and thereby limited, in nature and require complex post-fabrication assembly to integrate multiple materials or functional properties. That is, conventional approaches typically involve the separate fabrication of different sensing components (e.g., separate chemical sensing and electrical sensing elements) that are post-hoc assembled to provide some degree of integrated or co-localized functionality. Even in such scenarios, however, the components involved in the different types of sensing would typically be measuring different, but possibly proximate, sites, and thus may not be observing the same phenomena at a given time, particularly in instances where neural or neuro-muscular activity is being observed.

In contrast, the present approach employs a scalable, bottom-up microfabrication process in which different sensing and/or treatment modalities are grown, formed, or otherwise fabricated on a common platform. In certain such fabrication techniques, multiple materials that each provide differing functionality may be added to or otherwise used to functionalize different portions of a common probe base or template material. By way of example, in one implementation porous carbon templates are deposited or otherwise formed directly on dense arrays of electrical contacts to fabricate a sensor platform (or template). The individual templates (or groups of templates) may then be differently processed to form a dense array of different probe types, with each template corresponding to a probe. This provides three major differentiators relative to conventional approaches, including: 1) the direct (i.e., assembly-free) connection to high density electronic devices, 2) fabrication of dense and high aspect ratio probe templates (e.g., 5 micron-50 micron in diameter, but 0.2 mm to 2 mm long millimeters long), and 3) filling or impregnating the porous carbon templates with different materials yielding probe structures having different sensing capabilities or material properties. By way of example, the porous carbon templates can be filled with materials including, but not limited to: metals, ceramics, and polymers or hybrid polymers, providing flexibility in the choice of mechanical and electrical properties of the probes so formed. In this manner, simultaneous electrical and multianalyte chemical sensing and/or delivery may be provided in a single device capable of measuring at a single or overlapping site.

By way of further explanation, in one example of an implementation, three-dimensional (3D) carbon deposition technology (e.g., carbon nanotube templated—microfabrication (CNT-M)) is employed to allow fabrication of a sensing surface capable of both electrical and chemical sensing. Such a 3D carbon deposition process may be used to directly grow neural probes, each with different mechanical, electrical, and chemical properties, on a sensing substrate. This approach allows: (1) integration of electrical and chemical sensing modalities into a single sensor platform; (2) direct deposition of 3D neural probes on a high density electronic interface (i.e., no manual assembly for 3D recording in large scale neural networks); (3) hybrid neural electrode arrays with probes containing carbon, polymer, and metal features; and (4) a core fabrication process for controlling mechanical, electrical, and surface properties of neural sensors.

Figure 1B:
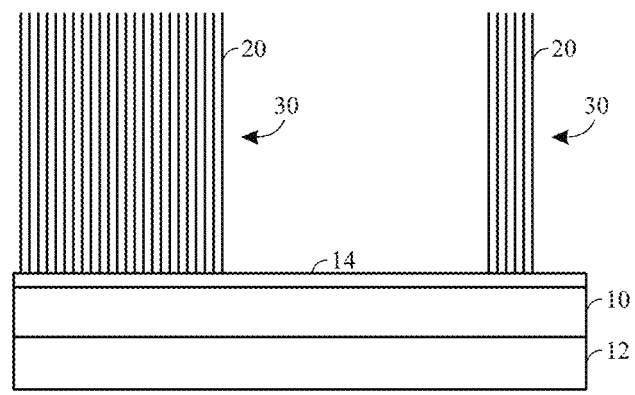
Figure 1C:
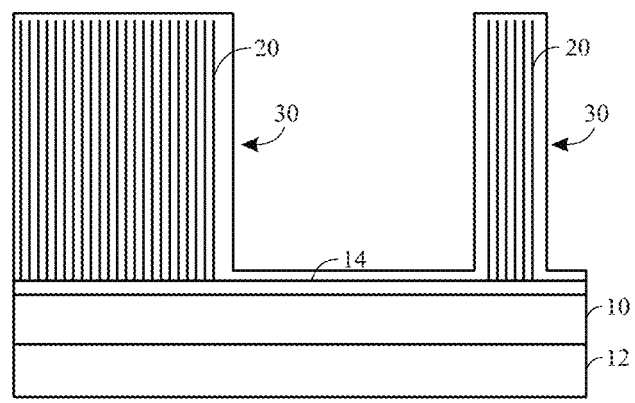

By way of introduction, FIGS. 1A, 1B, and 1C depicts a high-level visual flow of certain aspects of the CNT-M process related to growing carbon nanotube structures and infiltrating carbon as may be implemented with respect to the present approach. In the depicted example, the carbon nanotubes templates 30 are grown from patterned thin film catalysts. In one such approach, the pattern (which is used to outline the probe array) is formed through lithographic definition of one or more alumina/iron catalyst stacks or pads. By way of example, in the embodiment shown in FIG. 1A, a substrate of $SiO_2$ (layer 10) on Si (layer 12) is shown on which a layer 14 of $Al_2O_3$ (e.g., a 20-50 nm layer) is formed. Pads or stacks 16 (e.g., 4 nm Fe stacks) of Fe are formed on the layer 14, with nanotube 20 growth occurring on the stacks 16 (shown in FIG. 1B). The CVD-based carbon template growth in one such example uses ethylene (@ 750 C) and the height of the structures depends on iron thickness, deposition conditions, and growth time. Carbon structures greater than 2 mm tall can be grown by tuning the growth conditions. Lateral dimensions of the features (i.e., the carbon nanotube templates) are determined by the catalyst pattern, which may be patterned as small as 2-3 microns (for array of small probe pillars) or up to mm or cm width (for growth of large individual probes).

In FIG. 1C, the result of an additional CVD carbon infiltration step after carbon nanotube template growth (as discussed in greater detail below) is shown. The carbon infiltration may be performed on some or all of the fabricated templates 30 to help lock the carbon templates 30 into place for further processing, which may or may not include subsequent infiltration by other materials and/or metallization, depending on the probe type being formed. The infiltrated carbon can be very thin (maintaining the nanoporous template structure) or thick (fully filling the porous template to create carbon fibers/wires). This high temperature carbon infiltration step (and compatibility with electronic connectors/interfaces) is one aspect making hybrid carbon/metal structures. In particular, it is this step that cross-links the fragile porous carbon template together and provides robust handling during follow-on processes (e.g., electroplating, electropolymerization, and so forth).

Figure 2A:
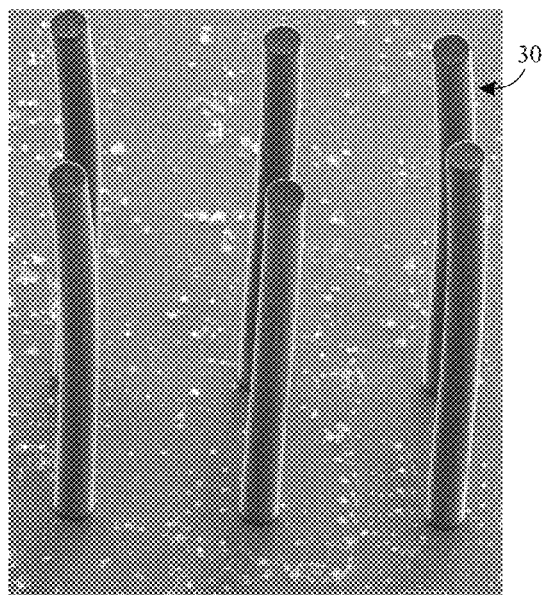
FIGS. 2A and 2B depict stages of a process for forming nanotube template structures with and without support structures, in accordance with aspects of the present disclosure.

As a further initial matter, in certain fabrication instances, mechanical stabilization of the high-aspect ratio nanotube template structures 30 may be employed as part of the CNT-M process. In particular, dimensional reliability of the template structures 30 can be influenced by catalyst thickness, patterned feature size, and carbon template height. Additionally, small variations in growth rate can lead to probe bending and templates 30 that are bent or otherwise not-straight for one or more of these reasons are shown in the FIG. 2A.

Figure 2B:
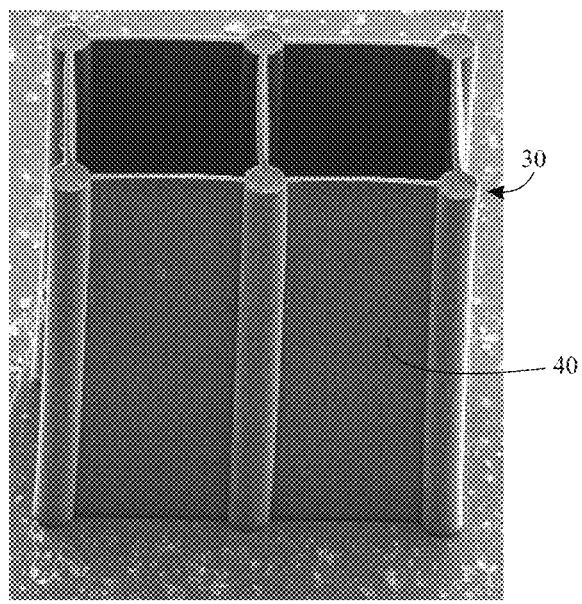

To address these issues, and as shown in FIG. 2B, in one embodiment sacrificial support structures 40 (e.g., support ribs) may be provided or incorporated between template structures 30 to keep the template structures 30 stable during processing. The support structures 40 may be removed (such as through directional or reactive ion etching) prior to subsequent processing steps where access to some or all of the template surfaces 30 is needed, such as prior to a subsequent metal plating step or infiltration step. The support structures 40, when employed, support the carbon template during deposition and growth. In one such embodiment, high density arrays of templates less than 20 μm in diameter are formed and, using the mechanical stability provided by support structures 40, grown to greater than 2 mm by tuning the growth parameters.

Figure 3:
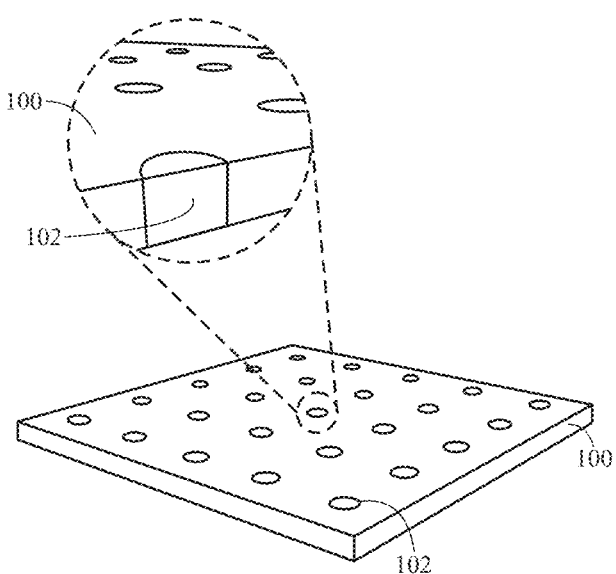
FIG. 3 depicts an electrical interposer used in a multimodal fabrication process, in accordance with aspects of the present disclosure.
Figure 4:
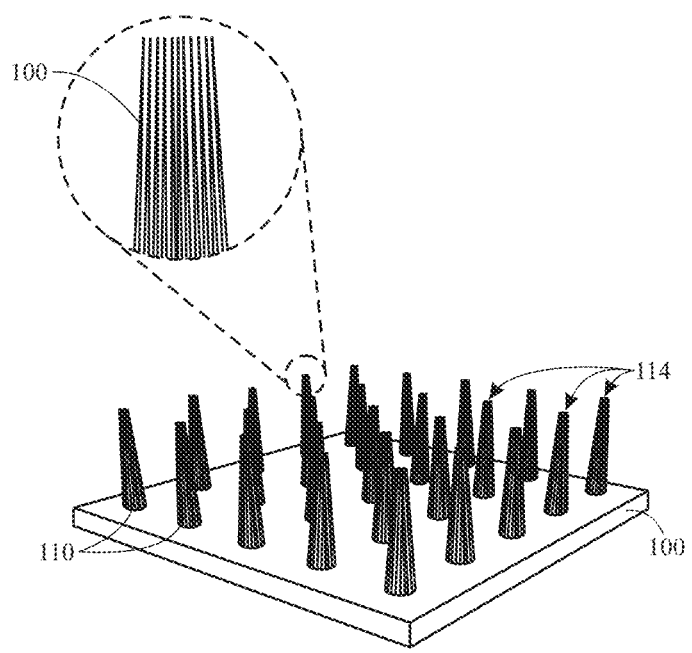
FIG. 4 depicts carbon nanotube template formation on the electrical contracts within interposer of FIG. 3, in accordance with aspects of the present disclosure.

The preceding relates various generalized aspects of carbon nanotube template fabrication using CNT-M processes. The following relates further aspects of how such fabrication processes, or comparable processes, may be leveraged to form a multimodal sensing system. An overview of one such approach is shown in FIGS. 3-4. In particular, the fabrication of an interface (e.g., a neural interface) utilizing a carbon deposition process (e.g., CNT-M, as discussed above) to directly grow arrays of probes on a 3D electronic interface is shown.

In accordance with this process, a substrate in the form of a high density electrical interface (i.e., an interposer 100) is initially provided, as shown in FIG. 3. In the depicted example, the interposer 100 includes a plurality of spaced apart conductive (e.g., metal) vias 102 that pass through the interposer 100 to provide electrically conductive pathways from one surface of the interposer 100 to an opposing surface. In addition, during the fabrication process described herein, the vias, during fabrication steps, may also serve as a high-temperature and conductive interface for growing carbon nanotube templates as discussed herein. By way of example, in one implementation a fused silica or sapphire substrate fabricated with gold-filled vias 102 may be employed as the interposer 100.

Turning to FIG. 4, 3D high-aspect ratio carbon templates are directly deposited (such as using a carbon nanotube template-microfabrication (CNT-M) technique, as discussed herein) on the interposer 100, such as on some or all of the vias 102 on one face of the interposer 100.

With respect to the CNT-M process in the present sensor fabrication context, this process is suitable for fabrication of high aspect ratio microelectromechanical systems (MEMS) and other 3D microstructures from silicon, silicon nitride, silicon dioxide, carbon, metal, and so forth. As described herein, in one implementation the CNT-M process starts by generation of a two dimensional catalyst pattern on a surface, here a via 102. This may be accomplished by a photolithographic patterning step of a metal catalyst used to initiate carbon nanotube growth. 3D vertically aligned carbon nanotube templates are subsequently grown from the catalyst pattern. In this manner, CNT-M process also allows integration of both nano- and microscale features within a neuroprobe fabricated via these processes, which presents advantages, and further versatility in electrode shape, geometry, and function as discussed herein. This process has been used to grow nanotube structures that are over 0.5 millimeters tall (extendable to >2 mm) with lateral pattern dimensions down to 2-3 microns, yielding aspect ratios greater than 200:1.

In the depicted example of FIG. 4, tapered nanowire groups 114 are deposited on or over the conductive vias 102, such as by using the respective vias 102 as nucleation points for the growth of the grouped carbon nanotubes or nanowires 110 associated with a given template. In one implementation, the carbon templates 114 are connected to respective vias 102 (or similar connecting trace or structure) using pulsed electroplating. The aggregated groups 114 of carbon nanotubes or nanowires 110 over each via 102 will, when processed as discussed herein, form an individually addressable probe with each resulting probe structure being addressable through the underlying conductive via 102.

In this example, the carbon nanotube groups 114 so formed each constitute a porous carbon template that allows infiltration or filling of the respective template with a range of materials, with different materials allowing different types of sensing or stimulation via the respective probe 120 so formed. Individual probes, groups of probes, or types of probes may also be metalized where appropriate for the functionality of that probe type. The infiltration step provides mechanical and electrical properties that resemble the "filler" (i.e., infiltrated) material, yet at aspect ratios that are unachievable using traditional microfabrication. By way of example, and turning to FIG. 5, each porous template (i.e., nanowire or nanotube group 114) may be functionalized by infiltrating or filling with one or more materials to form the respective probes 120. Such functionalization may be by chemical vapor deposition (CVD) (suitable for carbon infiltration), pulsed electroporating (suitable for metal infiltration), electropolymerization (suitable for polymer infiltration), or other suitable deposition of implantation techniques. The desired probes 120 that are selected for metal or polymer infiltration may be selected during the plating/polymerization process by connecting only the desired vias to the electrical contacts in the plating/polymerization bath. In such an approach, only those probes not selected for plating or polymerization will be available for infiltration with other materials (i.e., CVD).

Figure 5:
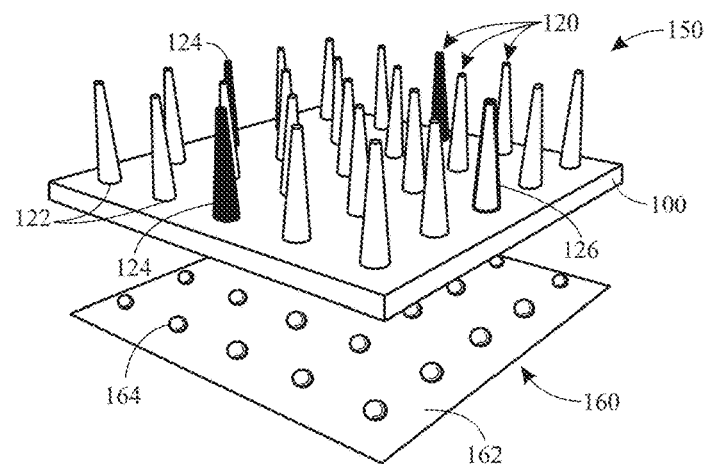
FIG. 5 depicts connection of an electronics interface to the interposer of FIG. 4 after infiltration of the templates to form a multimodal array of probes, in accordance with aspects of the present disclosure.

The filled or infiltrated templates 114 constitute probes 120 as discussed herein, with the sensing, stimulation, or chemical release characteristics of each probe 120 being determined by the material(s) infused into the 3D carbon template 114. By way of example, 3D carbon templates 114 may be filled or infiltrated with metal to facilitate sensing of electrical activity (probes 122), carbon to facilitate sensing of chemical activity (probes 124), and/or polymer (e.g., poly(3,4-ethylenedioxythiophene) polystyrene sulfonate (Pedot:PSS)) to facilitate release of one more chemicals (probes 126). While in certain implementations the filling or infiltration operations may be performed in an evenly distributed manner (i.e., creating equal numbers of each type of probe). Alternatively, as shown in FIG. 5, the number and/or spatial distribution of each type of probe 120 may be optimized or otherwise tailored to a particular type of operation or application, such as neural monitoring, with more of certain types of probes (e.g., electrical probes 122) being formed than others (e.g., chemical sensing probes 124 or chemical release probes 126). The relative sensitivity of different probe types and/or the spatial coverage needed for a given type of data (e.g., chemical or electrical) may be a factor in determining the relative number and/or distribution of probe types. The number and/or position of each type of probe 120 may be altered by selecting specific vias 102 to make electrically active within electroplating or electropolymerization baths, where only the vias that are selected (i.e. electrically contacted) will become infiltrated.

Figure 6:
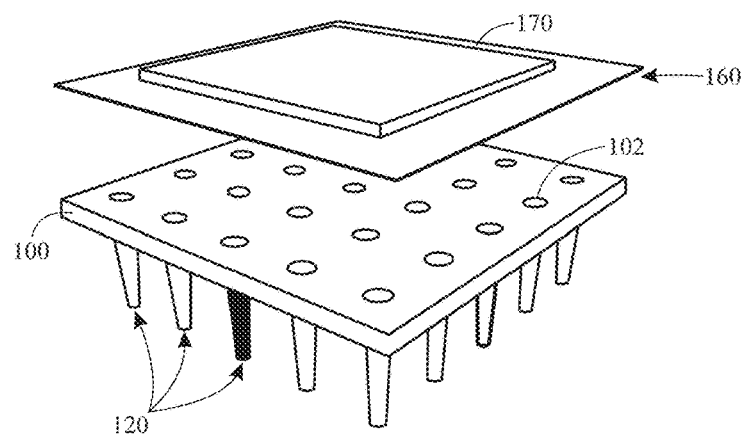
FIG. 6 depicts the interposer, probes and electronics interface of FIG. 5 from a different perspective.

Turning to FIGS. 5 and 6, after formation of the probes 120 (i.e., functionalized nanowire groups), the resulting 3D sensor assembly, i.e., probe array 150, may be connected to electronics by associating the interposer 100 with an electrically connective structure (e.g., a solder ball grid array (BGA) 160 formed from a substrate 162 and spaced apart solder ball structures 164). In such an assembly, the respective solder balls 164 are mated to respective via structures 102 to provide the ability to individually address each probe 120. As shown in FIG. 6, which depicts the assembly of FIG. 5 from a reversed perspective, the solder ball grid array 160 may, on the opposite side of the substrate from the solder balls 164, be attached to or otherwise connected to high density electronics 170 configured to communicate with the functionalized probes 120 through the solder balls structures 164 and associated vias 102. The high density electronics 170 may take the form of either high density wired connectors or wireless signal processing and communication electronics.

Figure 7:
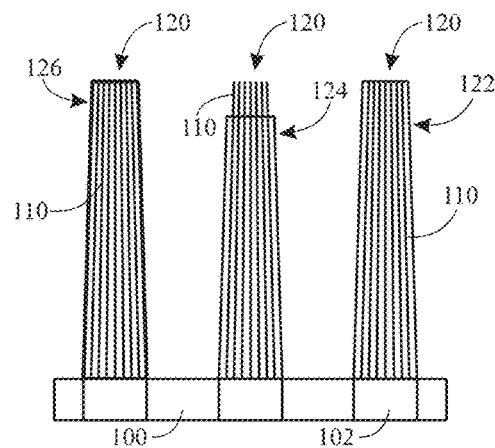
FIG. 7 depicts a side view of different probe types, in accordance with aspects of the present disclosure.

With the preceding in mind, FIG. 7 depicts a cut-away side view of three representative-types of functionalized probes 120 as discussed herein. As shown each probe 120 is formed on a via 102 that passes through an interposer 100 substrate. As may be appreciated, conventional lithographic fabrication technologies are typically limited to a narrow set of material substrates (i.e. silicon, parylene, polyimide, or silicone). Lack of material and process options has led to constraints on the minimal probe diameter (required for tissue penetration), the geometry and number of electrical sensors (along the probe shaft), and the type of electrical connection available to signal processing and communication electronics. However, a broader material set is available for microfabrication through the use of chemical vapor deposition (CVD), electroplating (e.g., aqueous liquid electroplating), and electropolymerization coating techniques as discussed herein. Extension of neural probe fabrication to these processes as applied to carbon nanotube templates 114 thereby increases the materials available for neural probe fabrication.

However, prior to the present approach, certain limitations have precluded the use of these processes for neural probe fabrication. First, CVD, electroplating and electropolymerization are typically thin film process, producing 13-130 nanometer layers of material. Therefore, these processes are incompatible with the production of large 3D structures. Second, CVD requires high processing temperatures, which lack compatibility with many of the support materials in the neural probe package and electrical interfaces. As may be noted from the preceding sections, these issues are addressed in the present approach through: (1) initial CVD deposition of vertical mm-scale porous carbon templates 114, which provide vertical scaffolds for extension of CVD, electroplating, or electropolymerization to relatively tall 3D structures; (2) use of a high temperature electronic interface for carbon template formation (e.g., via CNT-M) that remains compatible with conventional electronics packaging approaches; (3) use of pulse electroplating or electropolymerization for the creation of hybrid carbon/metal or carbon/polymer probes (e.g., via infiltration and filling of the original porous carbon template; and (4) fabrication of neural probe arrays with versatile shaft geometries (e.g., diameters ranging from 5 µm-130 µm).

Turning to the polymer infiltrated probe 126 shown in FIG. 7, this probe may be functionalized to release a chemical(s) or biomolecule(s) (e.g., dexamethasone, dopamine, and so forth) when electrically activated through respective via 102 (e.g., in response to an applied voltage).

One example of a suitable polymer is poly(3,4-ethylenedioxythiophene) polystyrene sulfonate (Pedot:PSS). In this example, in response to an applied voltage, the Pedot:PSS polymer releases one or more chemicals (e.g., neurotransmitters) attached to or otherwise held by the polymer matrix, one or more of which may be of interest in a neural monitoring/stimulation context. Examples of suitable chemicals for release include, but are not limited to small, charged molecules that can enter or release from the polymer matrix easily in response to controlled switching of electrode polarity (i.e., activation of a respective via 102).

By way of example, in one embodiment the infiltrated polymer matrix is loaded with dopamine. Loading of the matrix may be accomplished under mildly acidic conditions (pH 4.5-5) and include combining the dopamine with intermediate polymer stabilizers, such as polyvinylpyrrolidine (PVP) or polyethylene glycol (PEG).

With respect the carbon infiltrated probe 124, this probe may, in response to differential voltammetry, perform the function of sensing specific neurotransmitters. Further, the surface chemistry of the probe 124 may be controlled (such as via the carbon deposition process by which the templates are formed) for chemical (e.g., neurotransmitter) specificity. Thus, this functionalized probe 124 may provide a chemical sensing functionality useful in a neural or neuromuscular monitoring context. By way of example, carbon infiltrated probes 124 may be designed or configured for measuring (or otherwise sensing) the presence of chemicals of interest including, but not limited to, one or more of dopamine, serotonin, and/or ascorbic acid.

By way of further background into this aspect of chemical-sensing probe formation, free-standing carbon fibers have been shown capable of electrochemical detection of specific neurotransmitters within a background of similar chemicals. As electrochemical detection of neurotransmitters is a surface-based electrochemical approach, specificity is thought due to both the nanoporous structure and surface chemistry (—COOH at defect sites) of the nanofibers. However, despite the potential advantages of adding specificity to neurotransmitter electrochemical probes, utility of this technique has remained limited due to the difficulty of controlling the exact levels of surface defects during the nanofiber deposition processes.

The present approach, such as via use of the CNT-M process provides an additional level of control over the surface chemistry of the nanoporous carbon sensors used in chemical sensing. This is due to the presently described two-step process by which, after deposition, the carbon nanotube templates are infiltrated or filled with additional carbon. By controlling time and temperature parameters during carbon infiltration (i.e. carbon template filling) the surface chemistry of the resulting probes 124 may be adjusted. Thus, the infiltration step is useful in: (1) providing mechanical strength to the carbon nanotube templates during further processing in any electroplating and/or electropolymerization steps, and (2) controlling surface defects along the length of the carbon surface which may allow for chemical sensing sensitivity and/or selectivity.

By way of example, small grain layers of carbon may be added to the surface of a template during the carbon infiltration step. Such conformal layers may be a mixture of graphitic and amorphous carbon and provide additional control over defect sites, and therefore surface chemistry, of the template, that may in turn be leveraged to provide chemical (e.g., neurotransmitter) specificity. In this manner, the present fabrication approach should be capable of: (1) fabrication of hybrid neural probes with nano- and microscale features through selective infiltration of the porous carbon templates (i.e. some nano-features left unfilled), and (2) specific neurotransmitter sensing (e.g. dopamine vs. serotonin) based on control of the carbon nanotube template surface defects and functional chemistry.

With respect to the metal infiltrated or plated probe 122, this probe may perform a function of single unit (i.e. nerve) recording, effectively recording or monitoring electrical activity at the monitored site. The mechanism underlying this recording functionality may be spike sorting and/or local field potential measurement, which provide useful indications of underlying electrical events at the monitored site and may also be useful in a neural or neuromuscular monitoring context.

In practice, the metalized probe 122 may be formed initially as a carbon infiltrated probe, as discussed above with respect to chemical sensing. However, some portion of the carbon infiltrated probes may be selected for metallization, such as via electroplating with a conductive metal or metal alloy (e.g., a gold alloy). In such instances, electroplating may be facilitated by selective activation of those probes (or types of probes) to be electroplated using the individually addressable vias 102 beneath the probes 120. The metalized probes 122 so formed may then be used for monitoring electrical activity and/or for electrical stimulation (i.e. application of an electric field across the neural tissue by applying an electrical current between probes).

Figure 8:
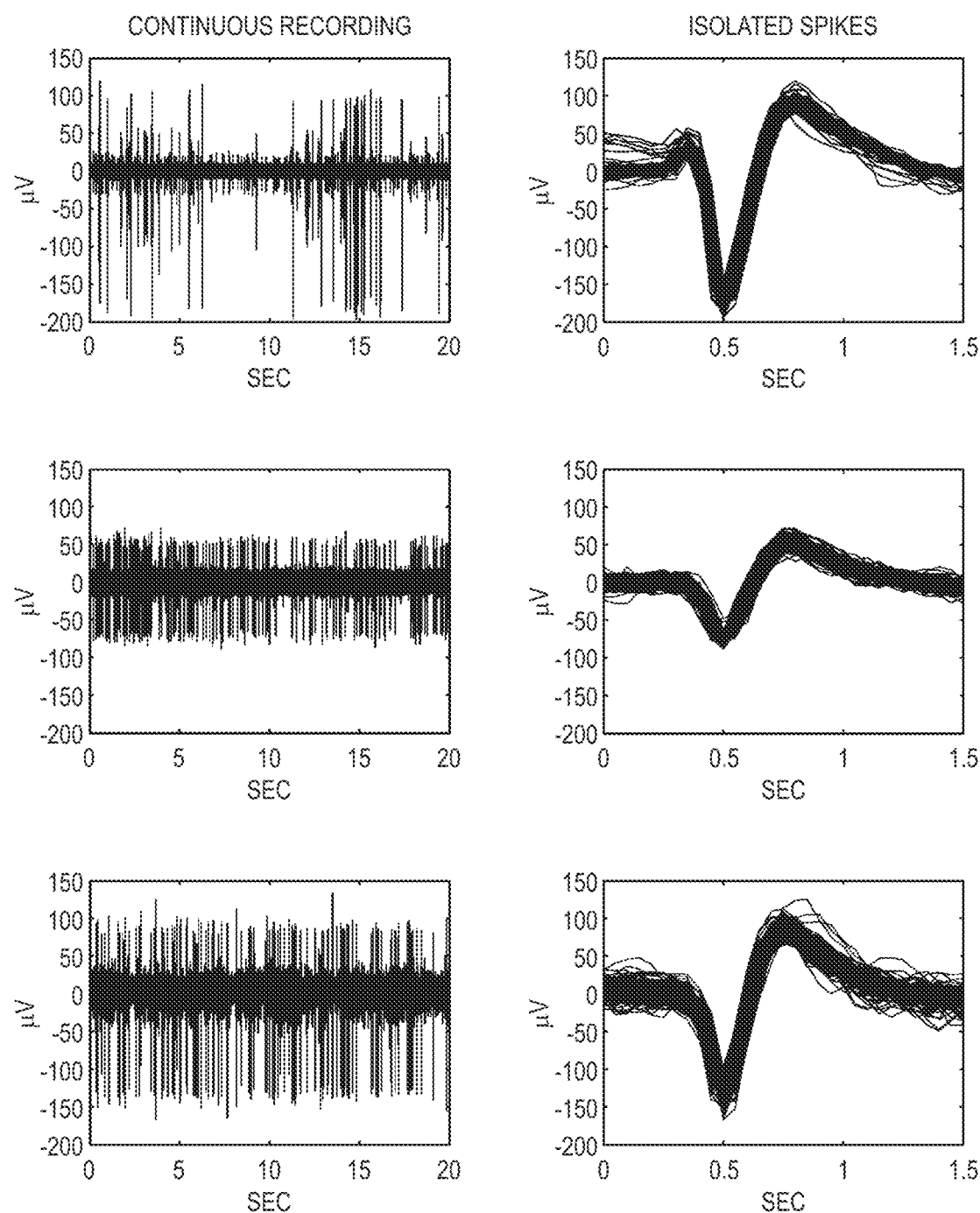
FIG. 8 depicts results of a study measuring electrical activity using a metal infiltrated recording probe within a multimodal probe array, in accordance with aspects of the present disclosure.

With the preceding in mind, a number of studies were performed testing the presently disclosed approach and device. In one such study, single unit nerve activity was recorded within the cortex of anesthetized mice. FIG. 8 shows results obtained in this study, with the topmost row showing neural recordings from ultrasmall (20 µm) electrodes using a gold alloy probe (coated with a conductive (PEDOT:PSS) polymer coating), which conducts both ionically and electronically and created a large surface area interface with the tissue. The PEDOT:PSS conductive polymer coating was electropolymerized on the probes after fabrication. Parylene-based insulation was applied to the probe structure, and laser-ablated at the tip to expose the electrical recording site. Electropolymerization of the exposed tip was performed by making electrical contact through the same electrical path used in recording. The middle and lower results show comparison electroneurograms using probes without the conductive polymer coating (middle row), and from standard tungsten electrodes (i.e., a 50 µm tungsten microwire) (bottom row). In these tests, probes fabricated using gold alloy and CNT-M probes as discussed herein penetrated the brain tissue with or without the dura intact.

Figure 9:
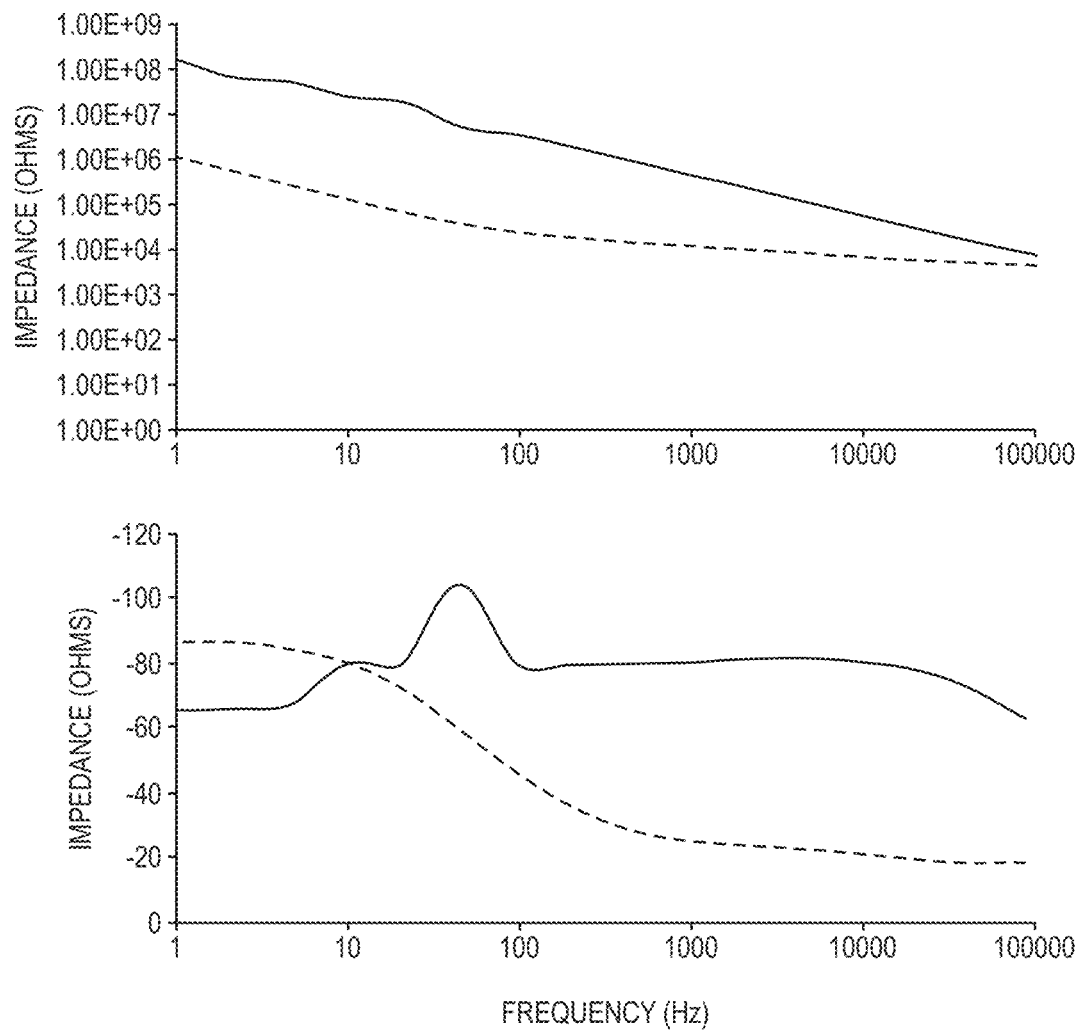
FIG. 9 graphically illustrates electrical characterization of a hybrid material probe, in accordance with aspects of the present disclosure.

FIG. 9 graphically illustrates electrical characterization of the gold neural probes before (blue lines) and after (red lines) coating with the PEDOT:PSS coating. Electrochemical impedance spectroscopy (EIS) was performed in room temperature PBS (pH 7.4) using a 3-electrode cell with a platinized titanium mesh counter electrode and Ag/AgCl reference electrode. The frequency was swept from 1 Hz to 100 kHz using a 5 mV RMS wave. The upper graph depicts EIS impedance values for the same probe before and after coating while the lower graph depicts EIS phase angle values for the same probe before and after coating. As shown, these results show significantly decreased impedance and electrode polarization when using coated (vs. uncoated) ultrasmall probes. These results demonstrate that the ability to apply multiple materials to probe structures within the array may be used to tailor electrical properties of the neuroprobe.

Another interesting aspect of the CNT-M process employed in this study is the capability to drastically alter the ratios of probe to coating. For example, the ultrasmall probes in this experiment were insulated with 4 µm thick layers of parylene, demonstrating another feature that may find utility in increasing the overall lifetime of electrical implants (i.e. longer protection against in vivo chemical damage of the polymer insulator).

Figure 10:
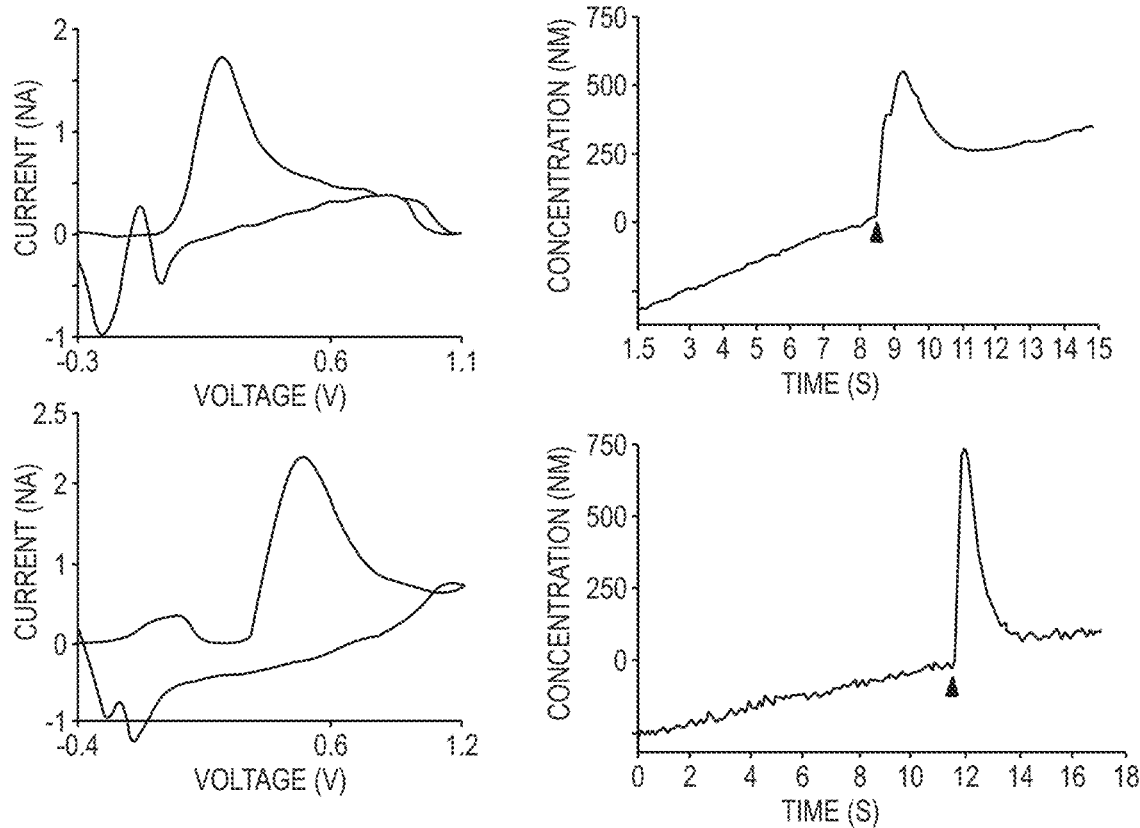
FIG. 10 depicts results of a study sensing neurotransmitters using a carbon infiltrated probe within the multimodal probe array, in accordance with aspects of the present disclosure.

In a further study, results of which are shown in FIG. 10, CNT-M carbon filled probes were utilized for in vitro neurotransmitter sensing. In this example, dopamine sensing was performed using a CNT-M carbon probe (i.e., carbon infiltrated). In the upper row of graphs, cyclic voltammetry was performed using a carbon probe. While the probe was in artificial cerebrospinal fluid (aCSF), a drop of 500 nM dopamine was delivered next to the probe. The time of dopamine delivery is indicated by the arrow head shown in the right-hand graph. The left-hand graph depicts a cyclic voltammogram directly after dopamine was delivered. The peak at 0.3 V is a signature of dopamine. The amplitude of this peak is proportional to dopamine concentration. The right-hand graph depicts the time course of the dopamine concentration obtained by monitoring the amplitude of this peak in time. The lower row of graphs shows similar traces obtained with a standard carbon fiber electrode in a mouse brain slice. Optogenetic stimulation of dopaminergic terminal in nucleus accumbens led to dopamine release with a peak concentration of about 700 nM (1s-long laser pulse (473 nm wavelength) at the arrow head shown in the right-hand graph). These results demonstrate that a carbon probe fabricated using a bottom-up approach, as discussed herein, is capable of measuring physiologically relevant concentrations of neurotransmitters at least as well as current or standard equipment).

Figure 11:
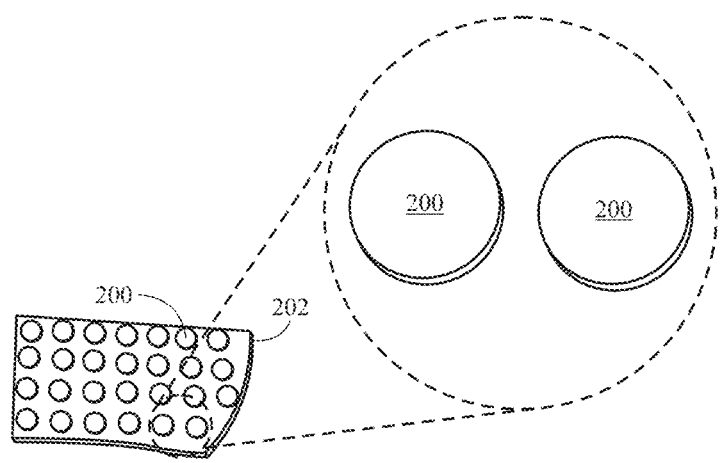
FIG. 11 depicts an embodiment of the invention in which a base substrate is separated from a fabricated structure to leave a carbon template and infiltrated materials available for implantation, in accordance with aspects of the present disclosure.

Turning to FIG. 11, an alternative embodiment to the present approach is depicted in which the CNT-M technique is used to fabricate structures with millimeter to centimeter lateral dimensions (e.g., in one embodiment 3 mm in diameter and 0.5 mm high). Here large disks probes arrays 200 formed of carbon infiltrated CNT templates grown on a substrate 202, e.g., a silicon substrate, are shown. This capability may be useful in expanding the fabrication process to applications in which larger probe structures are useful, such as in contexts employing large probes for deep brain stimulation). In FIG. 11 an array of 3 mm diameter discs 200 are shown on a silicon substrate 202 where the disks 200 were fabricated using the CNT-M process and subsequent carbon infiltration using CVD. In the depicted inset, a close-up view of a disk probe 200 is shown. Once carbon infiltration has occurred the disk probes 200 are mechanically robust, and can be removed from the underlying silicon substrate 202 (such that only the carbon template and infiltrated material remains). The separated probe disk 200 is then available for implantation.

Figure 12A:
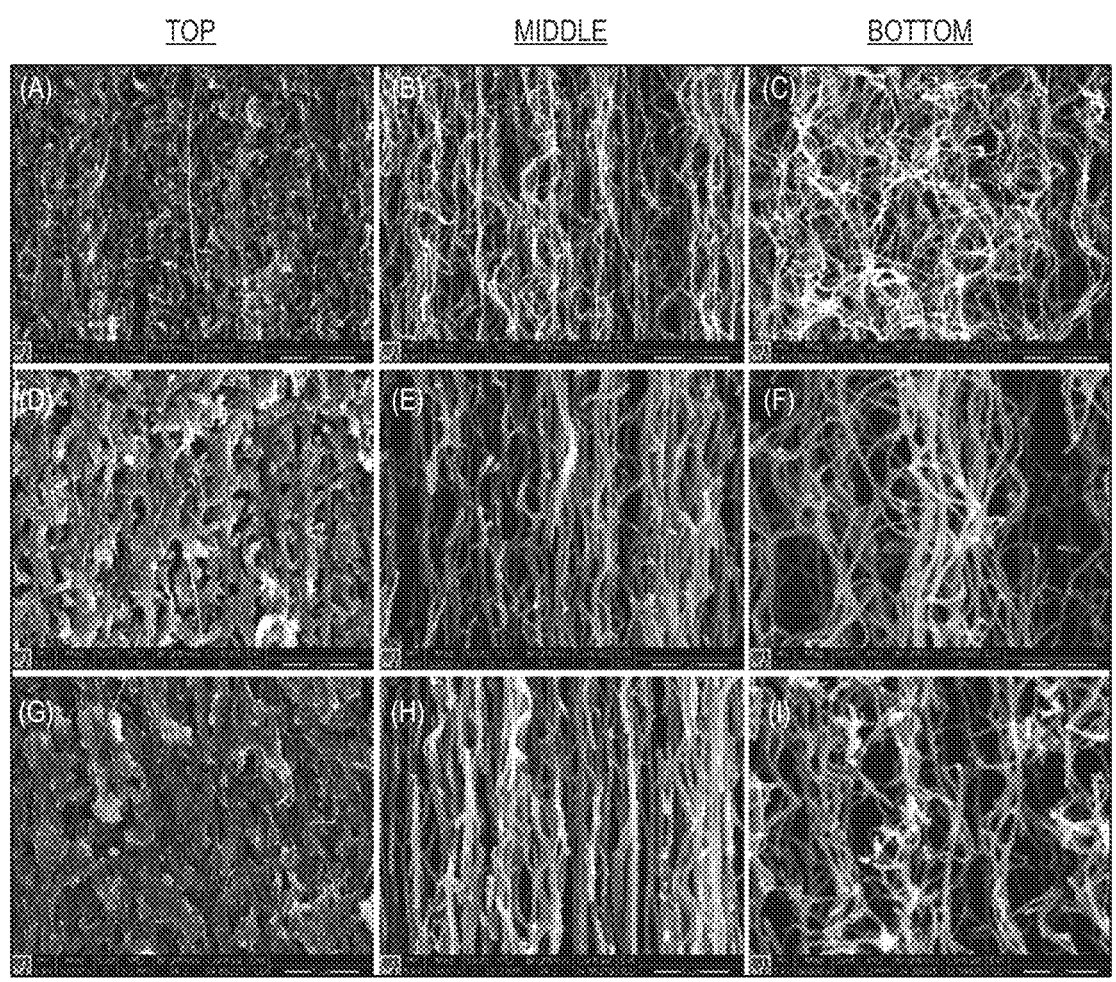
FIG. 12A depicts scanning electron microscopy (SEM) images of the separated disk structures of FIG. 11 after removal from the base substrate after 5, 10, or 15 minutes, respectively, of carbon infiltration via CVD, in accordance with aspects of the present disclosure.
Figure 12B:
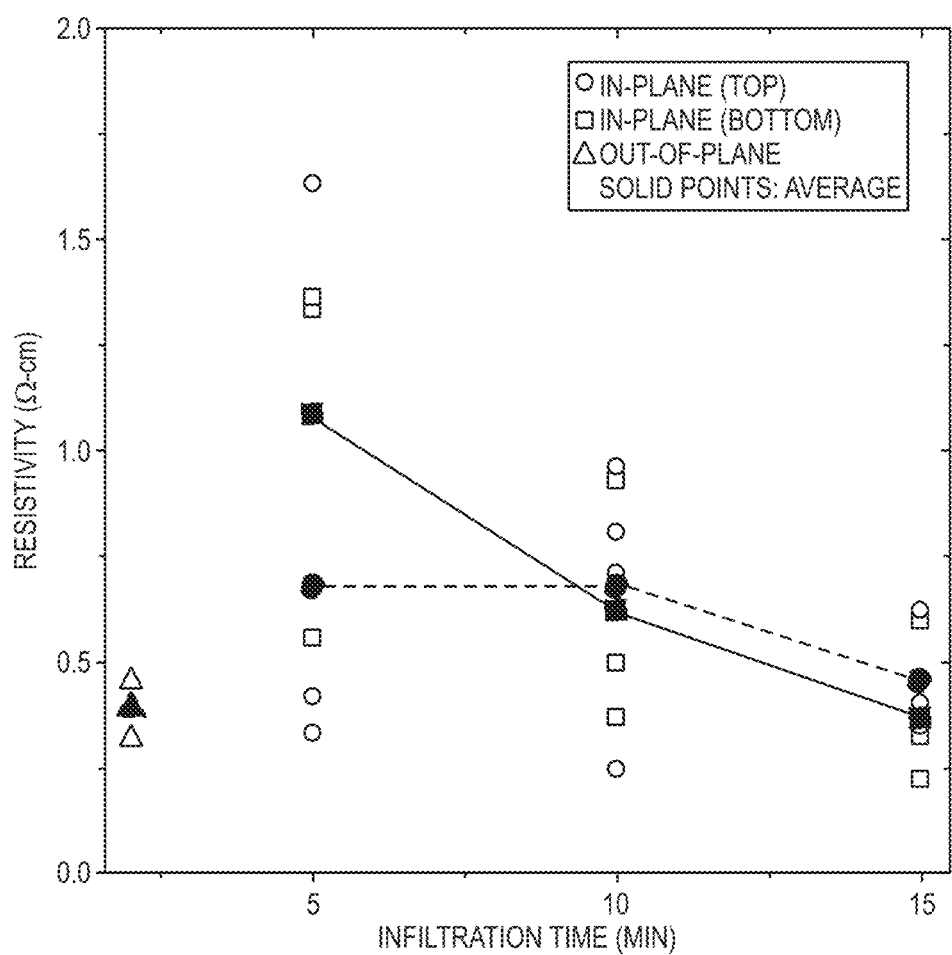
FIG. 12B depicts a graphical representation of electrical resistivity measurements made in different planes with respect to the separated disk structures, in accordance with aspects of the present disclosure.

Turning to FIGS. 12A and 12B, in FIG. 12A scanning electron microscopy (SEM) images are shown of the mechanically extracted CNT-M discs at different heights within the carbon infiltrated structures (i.e., probe disks 200). Carbon infiltration was for either 5 minutes, 10 minutes, or 15 minutes. In the depicted images, the images in the "Top" column are from a plane furthest from the substrate 202 during CVD) while those in the "Bottom" column are from the plane directly above the substrate during CVD. Images from the "Middle" column are from a plane between the top and bottom planes.

Turning to FIG. 12B, electrical resistivity measurements are shown that were made in different planes (with respect to the direction of the CNTs). Electrical resistance measurements were made of 3 mm diameter nanoporous carbon discs 200 and showed the ability to obtain resistivity of the nanoporous/infiltrated carbon probes that more closely match metals than standard amorphous or graphitic carbon fibers. As may be observed, there was an apparent decrease in resistivity with increasing infiltration time when resistivity was measured in-plane with the CNT structures. The lowest resistivity measurements were found for the out of plane condition and were measured using a similar CNT-M fabricated needle that was laid across a four point probe array. These numbers are consistent with literature results for CNT's along the tube direction.

Figure 13:
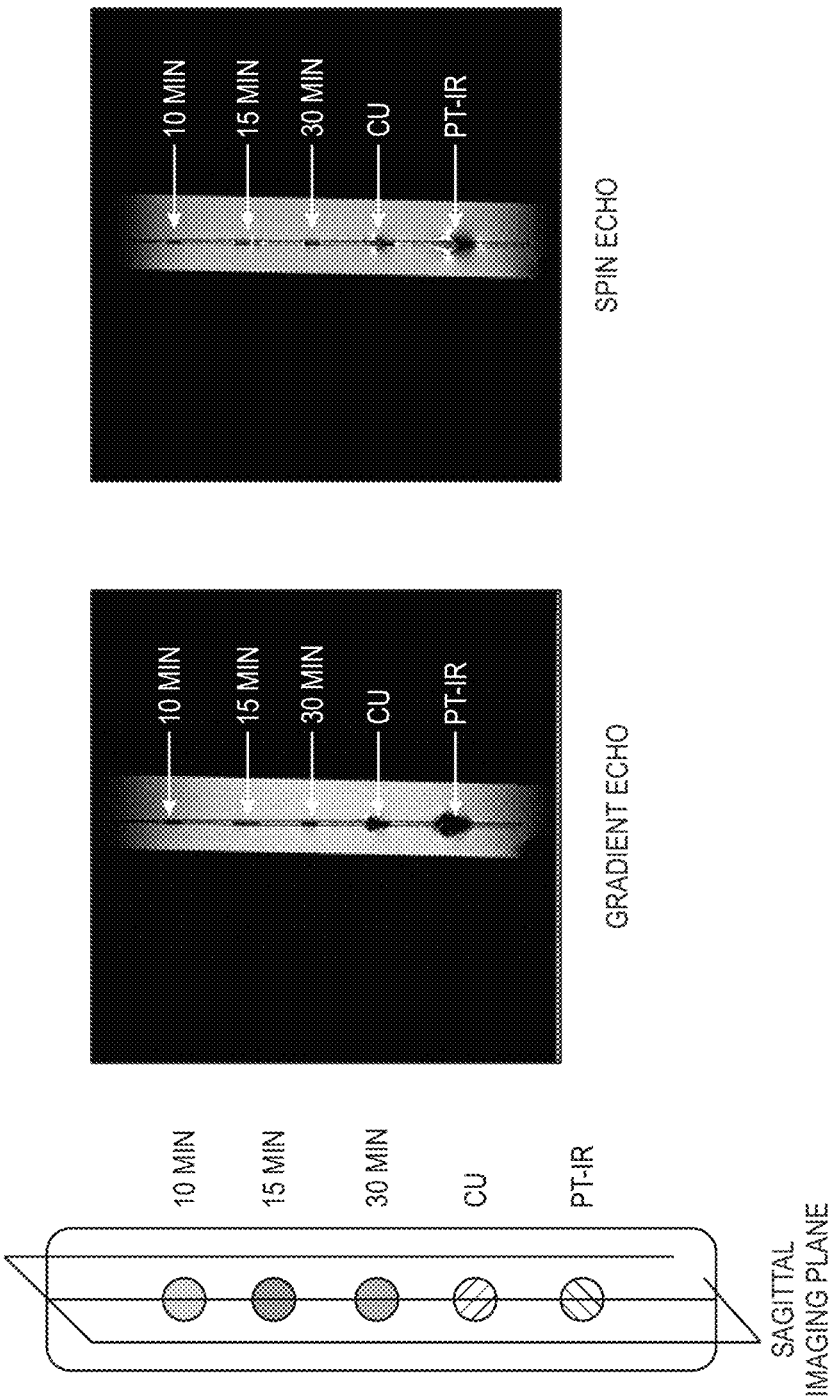
FIG. 13 depicts gradient or spin echo images from CNT-M discs after infiltration with carbon for 10, 15, or 30 minutes compared to copper or platinum iridium discs of equal size and after supporting the CNT, copper, and platinum iridium discs in water, in accordance with aspects of the present disclosure.

Turning to FIG. 13, this figure depicts gradient or spin echo magnetic resonance images from CNT-M discs 200 after infiltration with carbon for 10, 15, or 30 minutes compared to copper or platinum iridium (PtIr) discs of equal size. During imaging the disks 200 were supported in water using paper having a lightly adhesive backing. The MR images display the observed magnitude of the gradient and spin echo images acquired sagitally through the middle of the samples.

As shown in the in these figures, there are no significant distortions in the MR image around the CNT material, while both the copper and platinum iridium have significant artifacts. It should be noted that copper is the metal that most closely matches the magnetic susceptibility of human tissue; however, its use in implants is limited due to lack of biocompatibility. Platinum iridium is one the most used metal in neural implants due to both electrical characteristics and stability/chemical inertness.

Figure 14:
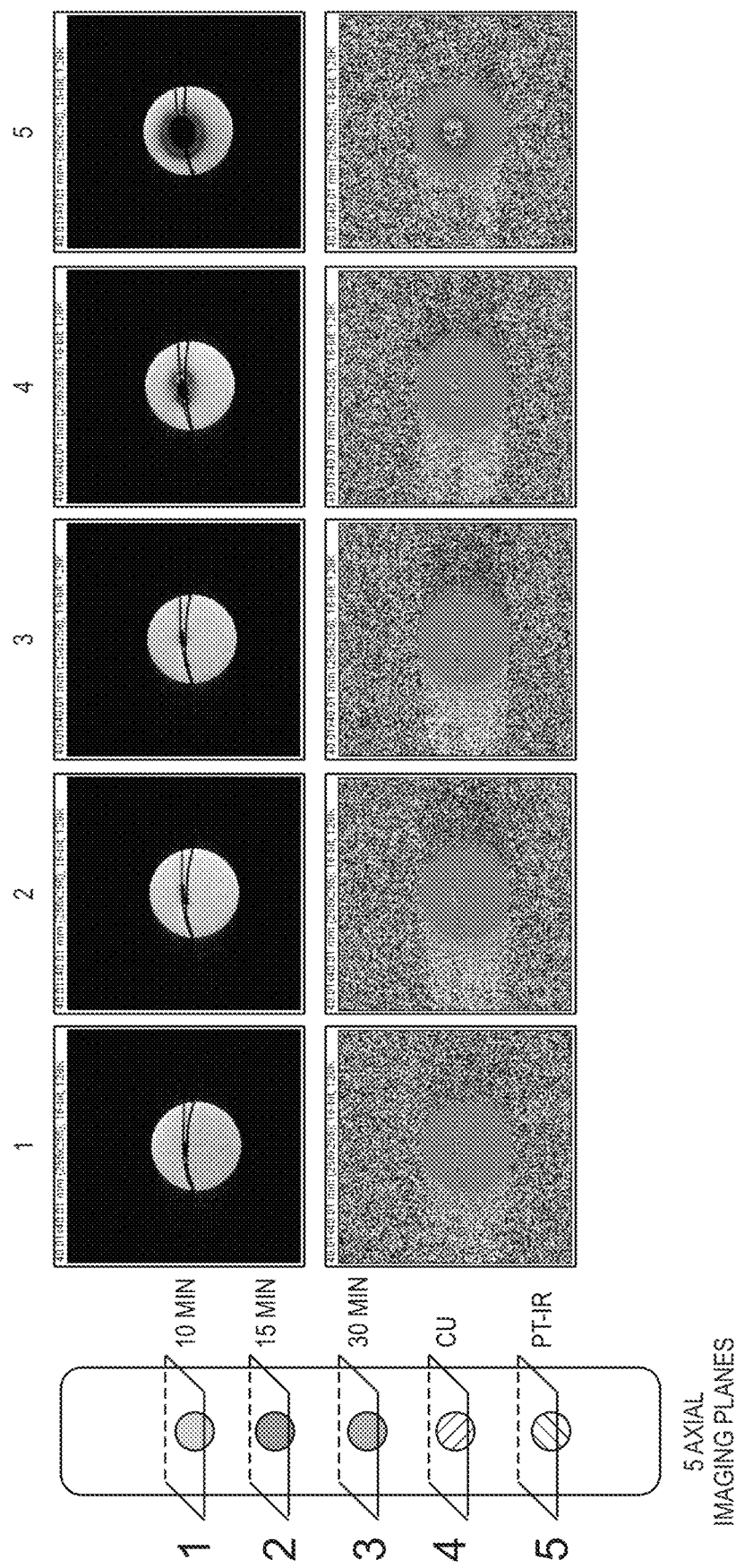
FIG. 14 depicts further characterization of the CNT discs using MRI after supporting the CNT, copper, and platinum iridium discs in water, in accordance with aspects of the present disclosure.

FIG. 14 depicts further characterization of the CNT probe discs 200 using MRI after supporting the respective probe disks 200, copper disk, and platinum iridium disk in water using paper having a lightly adhesive backing. The images display both the magnitude (top row of images) and Bo mapping (bottom row images) axially after acquisition with 1 kHz bandwidth.

Surprisingly, as shown in the images depicted in FIG. 14, the probe 200 images show that there is less than 10 Hz distortion from the nanoporous carbon material, matching results from the copper. Both the carbon nanotube probe disks 200 and copper show less distortion than the platinum iridium sample.

Figure 15:
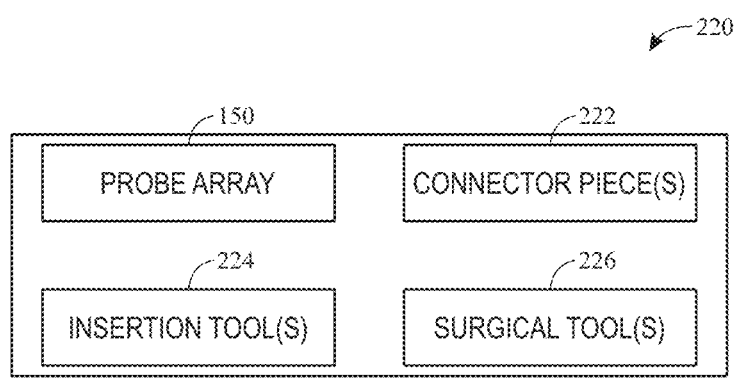
FIG. 15 depicts a block diagram of a kit for use in a medical procedure including a probe array in accordance with aspects of the present disclosure.

With the preceding probe array discussion in mind, FIG. 15 depicts an example of a kit 220 that may be provided for a respective medical or diagnostic procedure. In the depicted example, the kit 220 includes a probe array 150 (or alternatively a probe disk 200 as described above). The probe array 150 or disk 200 may be of a standardized configuration or may, in some implementations, be customized or tailored to an individual patient and/or procedure. The kit 220 may also include one or more connectors 222 suitable for connecting the probe array 150 or probe disk 200 to one or more respective medical devices, such as a monitor or other device suitable for reading signals form the probe array 150 or disk 200 and/or activating or powering the probes of the probe array 150 or disk 200. In the depicted example, the kit 200 also includes one or more surgical tools 226 that may be provided to facilitate a surgical operation or procedure involving the probe array 150 or disk 200. Similarly, one or more insertion tools 224 may be provided as part of the kit 220 that may be used to facilitate the insertion or attachment of a probe array 150 or probe disk 200 relative to a target tissue site. As may be appreciated, one or more included pieces of the kit 220 may be provided as a single-use or disposable unit. For example, one or more of the probe array 150 (or probe disk 200), connectors 222, insertion tools 224, and/or surgical tools 226 may be used once for a given procedure and then discarded.

Technical effects include fabricating and using a multi-modal sensor platform suitable for measuring neural activity within cortical (or other) sites, while having simultaneous knowledge and control of neurotransmitter levels. In one implementation a CNT-M process is used for sensor platform fabrication that allows direct deposition on high density electronic interfaces. Using the templates formed by the CNT-M approach, hybrid material probe arrays (i.e. carbon, metal, and polymer) may be formed that enable multimodal sensing capabilities. These probes may be used and implanted directly attached to the fabrication substrate, or mechanically removed and implanted with only the CNT and infiltrated materials. Furthermore, the electrical, mechanical, and magnetic properties of the neuroprobes may be tailored by infiltrating the carbon with a variety of materials. It is also shown that in some cases infiltration of the nanoporous carbon results in electrical, mechanical, or magnetic properties that are not predicted by the properties of the bulk materials alone; resulting in unique performance of the CNT-M probe. A significant example of this is the magnetic susceptibility of the carbon infiltration CNT probe, which closely matches that of water/human tissue (resulting in artifact-free MR images).

The invention claimed is:

1. A probe array structure, comprising:
    a plurality of probes, wherein each probe comprises a carbon nanotube template, wherein some or all of the probes of the plurality of probes have a magnetic susceptibility matched to biological tissue;
    a first subset of the plurality of probes, wherein the first subset of probes is functionalized with a first material or set of materials such that, when in use, the first subset of probes senses a first physiological property of an underlying tissue or stimulates the underlying tissue; and
    a second subset of the plurality of probes different from the first subset, wherein the second subset of probes is functionalized with a second material or set of materials such that, when in use, the second subset of probes senses a second physiological property of the underlying tissue or stimulates the underlying tissue.

2. The probe array structure of claim 1, wherein each probe of the plurality of probes is individually addressable.

3. The probe array structure of claim 1, further comprising:
    a substrate on which the plurality of probes are formed; and
    one or more electrically conductive vias present in the substrate, wherein each probe of the plurality of probes is formed on a respective via.

4. The probe array structure of claim 1, wherein the first material or set of materials and the second material or set of materials are drawn from a set of materials comprising one or more of metals, ceramics, carbon, and polymers or hybrid polymers.

5. The probe array structure of claim 1, wherein the first subset of probes senses the first physiological property or stimulates the underlying tissue using an electrical property and the second subset of probes senses the second physiological property or stimulates the underlying tissue using a non-electrical property.

6. The probe array structure of claim 5, wherein the non-electrical property comprises one or more of chemical activity or reactivity, mechanical motion, acoustics, or vibration.

7. The probe array structure of claim 1, wherein the probe array structure comprises a neural probe array.

8. The probe array structure of claim 1, wherein the carbon nanotube templates are 2 microns to 50 microns in diameter and 0.2 mm to 2.0 mm in length.

9. The probe array structure of claim 1, wherein the carbon nanotube templates have an aspect ratio of 200:1 or greater.

10. The probe array structure of claim 1, further comprising:
one or more additional subsets of the plurality probes, wherein each additional subset of probes is functionalized with a different material or set of materials than the first subset and second subset such that, when in use, each additional subset of probes senses an additional physiological property of the underlying tissue or stimulates the underlying tissue.

11. A probe array structure, comprising:
a plurality of probes, wherein each probe comprises a functionalized carbon nanotube template and wherein each probe is individually electrically addressable such that the activation of each probe is independent of the other probes of the plurality of probes, wherein some or all of the probes of the plurality of probes have a magnetic susceptibility matched to biological tissue.

12. The probe array structure of claim 11, wherein the plurality of probes comprises different subsets of probes, each subset functionalized differently such that, when in use, the differently functionalize subsets sense physiological parameters or stimulate an underlying tissue using different principles.

13. A probe array structure, comprising:
a plurality of probes, wherein each probe comprises a carbon nanotube template and wherein some or all of the probes have a magnetic susceptibility matched to biological tissue, wherein the probe array structure, when imaged in a magnetic resonance imaging system, produces less than 10 Hz distortion.

14. A probe kit, comprising:
a probe array comprising a plurality of individually addressable carbon nanotube probes, each carbon nanotube probe functionalized to sense a physiological property of an underlying tissue or stimulates the underlying tissue when in use, wherein the probe array, when imaged in a magnetic resonance imaging system, produces less than 10 Hz distortion;
one or more connector pieces configured to interface the probe array with a respective medical device;
one or more insertion tools configured to facilitate the placement of the probe array to a target tissue; and
one or more surgical tools suitable for performing a surgical procedure for insertion of the probe array.

15. The probe kit of claim 14, wherein one or more of the probe array, the connector pieces, the insertion tools, or the surgical tools are disposable.

16. The probe array structure of claim 1, wherein the plurality of probes comprise carbon nanotubes templates having the magnetic susceptibility matched to biological tissue.

17. The probe array structure of claim 16, wherein the plurality of probes extend from a substrate.

18. The probe array structure of claim 17, wherein the substrate comprises a high density electrical interface.

* * * * *